US007289916B2

(12) United States Patent
Drnevich et al.

(10) Patent No.: US 7,289,916 B2
(45) Date of Patent: Oct. 30, 2007

(54) METHOD AND APPARATUS FOR MEASURING PROPERTIES OF CONCRETE

(75) Inventors: Vincent P. Drnevich, West Lafayette, IN (US); Xiong Yu, Cleveland, OH (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 11/067,867

(22) Filed: Feb. 28, 2005

(65) Prior Publication Data

US 2005/0210995 A1    Sep. 29, 2005

Related U.S. Application Data

(60) Provisional application No. 60/547,846, filed on Feb. 26, 2004.

(51) Int. Cl.
  *G06F 19/00*    (2006.01)

(52) U.S. Cl. .......................... 702/43; 702/53; 702/138; 702/189

(58) Field of Classification Search .................. 702/43, 702/53, 66, 138, 189; 73/19.08, 73, 788–790; 324/694; 338/35; 340/602; 700/208
See application file for complete search history.

(56) References Cited

U.S. PATENT DOCUMENTS

| 2,647,394 | A | * | 8/1953 | Schaeperklaus | ............. 73/32 R |
| 2,821,079 | A | * | 1/1958 | Kerridge | .................... 73/54.03 |
| 4,186,592 | A | * | 2/1980 | Eirich et al. | ................... 73/73 |
| 4,853,614 | A | * | 8/1989 | Carver | ........................ 324/664 |
| 5,136,249 | A | | 8/1992 | White et al. | |
| 6,215,317 | B1 | | 4/2001 | Siddiqui et al. | |
| 7,000,458 | B2 | * | 2/2006 | Sogo et al. | ..................... 73/73 |
| 7,038,470 | B1 | * | 5/2006 | Johnson | ..................... 324/664 |
| 7,040,145 | B2 | | 5/2006 | Drnevich et al. | |

OTHER PUBLICATIONS

Qiwei et al., 'Measurement of the Electromagnetic Constants of Concrete Materials by Time-Domain Reflectrometry', 2002, IEEE Publicaiton, pp. 230-233.*

(Continued)

*Primary Examiner*—Hal Wachsman
*Assistant Examiner*—Elias Desta
(74) *Attorney, Agent, or Firm*—William F. Bahret; P. Derek Pressley

(57) ABSTRACT

Methods and apparatus using time domain reflectometry to determine electrical properties of concrete for calculating physical and mechanical properties of the concrete that are indicative of concrete quality and durability. The dielectric constant of a concrete is determined to calculate the gravimetric water content of the concrete for use in finding the water-cement ratio of the concrete. Electrical conductivity of curing concrete is determined to calculate compressive strength of the concrete for use in predicting strength development in the concrete.

15 Claims, 8 Drawing Sheets

OTHER PUBLICATIONS

Wilson et al., 'Variations in the electrical properties of concrete with change in frequency', Sep. 1990, IEEE Publication, vol. 137, No. 5, pp. 246-254.*

Shakhtakhtinsky, 'The Effect of Porosity on the Electric Strength of Heat-resistant Concrete', Dec. 1997, IEEE Publication, vol. 4, No. 6, pp. 813-815.*

Malhotra, 'Evaluation of the Windsor Probe test for Estimating compressive strength of conrete', 1974, Doe Canada, vol. 7, No. 37, pp. 3-15.*

Rao, P.P., An ultrasound device for nondestructive testing of oilwell cement at elevated temperatures and pressures, JPT, Nov., 1982, 2611-2615.

Brameshuber, W. and Brockmann, A. T., Electrical conductivity measurements to characterize the setting and hardening of mortars, International Symposium (NDT-CE 2003), Non-Destructive Testing in Civil Engineering 2003.

Boast, W.B., A Conductometric Analysis of Portland Cement Pastes and Mortars and Some of Its Applications, Journal of the American Concrete Institute, vol. 33, 1936, 131-142.

Tamás, F.D., Electrical Conductivity of Cement Pastes, Cement and Concrete Research, vol. 12, No. 1, 1982, 115-121.

McCarter, W.J. and Curran, P.N., The Electrical Response Characteristics of Setting Cement Paste, Magazine of Concrete Research, vol. 36, No. 126, 1984, 42-53.

Perez-Pena, M., Roy, D.M., and Tamás, F.D., Influence of Chemical Composition and Inorganic Admixtures on the Electrical Conductivity of Hydrating Cement Pastes, J. of Materials Research, 4, No. 1, 1989, 215-221.

El-Nein, S.A. Abo, Kotkata, M.F., Sadd, M. and Razek, M. M. Abd El, Electrical conductivity of concrete containing silica fume, Cement and Concrete Research, vol. 25, No. 8, 1995, 1615-1620.

Garboczi, E.J., Schwartz, L. M. and Bentz, D.P., Modeling the influence of the interfacial zone on the DC electrical conductivity of mortar, Advanced Cement Based Materials, vol. 2, No. 5, 1995, 169-181.

Ramo, S., Whinnery, J. R. and Van Duzer, T., Fields and Waves in Communication Electronics, 1st ed., John Wiley, New York, 1965.

Fellner-Feldegg, J., The Measurement of Dielectric in the Time Domain, J. Phys. Chem., vol. 73, 1969, 612-623.

Topp, G. C., Davis J. L. and Annan, A. P., Electromagnetic determination of soil water content: Measurements in coaxial transmission lines, Water Resource Research, vol. 6, No. 3, 1980, 574-582.

Yu, X, Drnevich, V.P. and Olek, J., Time Domain Reflectometry for measuring water cement ratio of concrete, Paper accepted by the Proceedings of the 2004 International Symposium: Advances in Concrete through Science and Engineering, 2004.

Dalton, F. N., Herkelrath, W. N., Rawlins, D. S., and Rhoades, J. D., Time-domain Reflectometry: Simultaneous Measurement of Soil Water Content and Electrical Conductivity with a Single Probe, Science, vol. 224, 1984, 989-990.

Hausmann, M.R., Engineering Principles of Ground Modification, McGraw-Hill Publishing Co., 1990, 632p.

Garboczi, E. J. and Bentz D. P., Microstructure-property relationships in concrete: from nanometers to centimeter, 2nd Canmet/ACI Advances in Concrete Technology, International Symposium, Malhotra, V. M. Ed., 1995.

Kishi, T and Maekawa, K., Multi-component model for hydration heating of Portland cement, translation from Proceedings of JSCE, vol. 29, No. 526, 1995.

Preece S. J., Billingham J., and King A. C., On the initial stage of cement hydration, Cem. Tex, Kluwer Academic Publishers, 2000, 16-34.

Beek, A. van, Breugel K. van and Hilhorst, M.A., In-situ monitoring system based on dielectric properties of hardening concrete, Structural Faults and Repair, vol. 4, 1997, 407-414.

Malhotra, V.M., Testing hardened concrete: nondestructive methods, Ames: Iowa State University Press, 1976.

McCarter, W.J., The fractal surface of cementitious materials determined by impedance spectroscopy, Advances in Cement Research, Oct. 1994, vol. 6 No. 24, 1994, 147-154.

Gu, P., Xie P., Beaudion J.J., Some Applications of AC Impedance Spectroscopy in Cement Research, Cement Concrete and Aggregates, vol. 17, No. 2, 1995, 113-118.

Beck, A. van, Breugel K. van, and Hilhorst, M.A., Monitoring the hydration in LWA-concrete by dielectric measurements, 5th International Symposium on Utilization on High Strength / High Performance Concrete, 1999, 1007-1016.

Heimovaara, T. J., Frequency analysis of time domain reflectometry waveforms: 2. A four-component complex dielectric mixing model for soils, Water Resource Research, vol. 30, No. 2, 1994, 201-209.

Lin, C. P., Time Domain Reflectometry for soil properties, PH.D. Thesis, School of Civil Engineering, Purdue University, West Lafayette, IN, 1999.

Yasar, Y. E., Erdogan, Y. and Alaettin K., 'Effect of limestone aggregate type and water-cement ratio on concrete strength', Material Letters, vol. 58, No. 5, (2004) 772-777.

Fu, X. and Chung D.D.L. 'Improving the bond strength between steel rebar and concrete by increasing the water/cement ratio', Cement and Concrete Research, vol. 27, No. 12, (1997) 1805-1809.

Lydon, F.D., 'Effect of course aggregate and water/cement ratio on intrinsic permeability of concrete subject to drying', Cement and Concrete Research, vol. 25, No. 8, (1995) 1737-1746.

Boyd, A. J.and Mindness, S., 'The use of tension to investigate the effect of W/C ratio and cement type on the resistance of concrete to sulfate attack', Cement and Concrete Research, 34 (2004) 373-377.

Wisconsin DOT, 'Field measurement of water-cement ratio for Portland cement concrete - phase II field evaluation and development', Report No. 0092-45-16, Jun. 2002.

Popovic, S. and Popovic, J.S., 'Ultrasound testing to determine water-cement ratio for freshly mixed concrete', ASTM Journal of Cement, Concrete and Aggregates, vol. 20, No. 2,(1998) 262-268.

O'Connor, K. M. and Dowding, C. H. 'Geomeasurements by pulsing TDR cables and Probes', (CRC Press LLC, 1999).

Noborio, K., 'Measurement of soil water content and electric conductivity by time domain reflectometry: a review', Computers and Electronics in Agriculture, 31, (2001) 213-237.

Jones, S.B., Wraith J.M. and Or. D., 'Time Domian Reflectometry measurment principles and applications', Hydrology Process, No. 16, (2002) 141-153.

Siddiqui, S.I., Drnevich, V.P., and Deschamps, R.J., 'Time Domain Reflectometry development for use in geotechnical engineering', Geotechnical Testing Journal, GTJODJ, vol. 23, No. 1, (2000) 9-20.

Ezquerra, T.A., Kremer, F., and Wegner, G., 'AC electrical properties of insulator-conductor composites', In: Pier 6, 'Progress in Electromagnetics Research: Dielectric Properties of Heterogeneous Materials', Ed. A. Priou (Elsevier Pub Co., New York, 1992) 273-301.

Haldavnekar, V., Bobet, A., Santagata, M., and Drnevich, V., 'Soil treatment with a thixotropic fluid:an autoadaptive design for liquefaction prevention', Accepted for publication in the Proc. 11th International Conference on Soil Dynamics and Earthquake Engineering, Berkeley, CA, 2004, 8p.

Yu, X., Drnevich V.P. and Olek, J., 'Predicting strength development of concrete by Time Domain Reflectometry', Paper accepted by the Proceedings of the 2004 International Symposium: Advances in Concrete through Science and Engineering.

Korhonen et al., "Time-Domian Reflectometry of Water Content in Portland Cement Concrete," U.S. Army Corps of Engineering Cold Regions Research & Engineering Laboratory Special Report 97-27, Nov. 1997.

Hansen et al., "Determination of Liquid Diffusivity Using Single Point Moisture Content Measurements and Boltzmann's Transformation," 6th Nordic Symposium on Building Physics, Trondheim, Norway, Jun. 2002, 8 pgs.

Hansen et al., "TDR Measurement of Moisture Content in Aerated Concrete," 6th Nordic Symposium on Building Physics, Trondheim, Norway, Jun. 2002, 8 pgs.

Hager et al., "Monitoring of cement hydration by broadband time-domain-reflectometry dielectric spectroscopy," Journal of Applied Physics, vol. 96, No. 9, 5117-5128.

Siddiqui, S. I., Drnevich, V. P., "Use of Time Domain Reflectometry for Determination of Water Content and Density of Soil," Project No. Indiana HPR 2094, Joint Highway Research Project, Indiana Department of Transportation and Federal Highway Administration, Aug. 13, 1995, 271 pgs.

White, I., Zegelin, S.J., Topp, G.C., "Effect of Bulk Electric Conductivity on TDR Measurement of Water Content in Porous Media," Symposium and Workshop on Time Domain Reflectometry in Enviromental, Infrastructure, and Mining Applications, Northwestern University, Evanston, Illinois, 1994.

ASTM D6780-05, Standard Test Method for Water Content and Density of Soil in Place by Time Domain Reflectometry (TDR), © 2005 ASTM International.

Drnevich, V.P., Yu, X., and Lovell, J., "Beta testing implementation of the Purdue Time Domain Reflectometry (TDR) method for soil water content and density measurement," Final Report, Report No.: FHWA/IN/JTRP-200-20, Joint Transportation Research Program, Indiana Department of Transporation - Purdue University, 2003, 256 pgs.

* cited by examiner

METHOD AND APPARATUS FOR MEASURING PROPERTIES OF CONCRETE

CROSS-REFERENCE TO RELATED APPLICATION

This application claims the benefit of U.S. Provisional Patent Application Ser. No. 60/547,846, filed Feb. 26, 2004, which application is hereby incorporated by reference along with all references cited therein.

TECHNICAL FIELD OF THE INVENTION

The present invention relates generally to methods and apparatus for measuring properties of concrete and, more particularly, to methods and apparatus for measuring electrical properties of concrete.

BACKGROUND OF THE INVENTION

Predicting behavior of concrete through preliminary analysis of concrete properties is important for construction operation decisions. Conventional approaches for evaluating properties of concrete in the field are often inaccurate, destructive, time consuming, and costly. Two important ways of evaluating concrete are measuring the water-cement ratio of the concrete mixture prior to placement and measuring the compressive strength of the concrete at certain introductory time intervals to predict long term strength and durability.

Water-cement ratio is an important property for concrete strength and durability so getting reasonably accurate measurements of it for freshly mixed concrete is of great practical importance. The current field practice to estimate water-cement ratio is from batch mixture quantities, i.e., water-cement ratio is calculated from the amount of water and the amount of cement added to the mixture. The estimated results are not generally found accurate, as the quantities do not accurately account for factors such as moisture contained in aggregate or water added at the job site.

Given the practical importance of water-cement ratio, many techniques have been proposed to measure this property. These generally involve measurement of water content and measurement of cement content. Field experiences indicate that accurate measurement of the water-cement ratio of fresh concrete is very difficult to achieve and currently there are no fast and reliable technologies available. For example, the nuclear gauge, which is widely used for quality control of soil compaction, is found ill suited for field water-cement determination use due to its unsuitability for igneous aggregates, poor field performance with limestone aggregates, and extensive training and certification procedure for operators. Several ultrasonic research tests have also been proposed. However, although the research unveiled some potential application of ultrasonic technology in fresh concrete characterization, none of the approaches produced satisfactory solutions for the instantaneous determination of the water-cement ratio. Accordingly, there still remains a need for a technique that more accurately measures the water-cement ratio in a shorter period of time to improve quality control and quality assurance of concrete.

Compressive strength of concrete is an important factor that controls the service life of concrete structures. Measurement of concrete strength development is important for quality assurance and quality control. The direct way to evaluate concrete strength is from laboratory compression tests performed on batch samples obtained in the field. The process is time consuming and the strengths obtained are generally not representative of the behavior of concrete in the actual structure due to difference in curing conditions. It is not uncommon to obtain significant scattering of measured concrete strength from compression tests on cylinders. Besides, the tests can only be performed to obtain concrete strength at fixed time since the tests are destructive.

Alternative approaches exist which are based on correlating concrete strength to other properties that can be measured more easily and nondestructively. An important characteristic of concrete strength is that it increases with curing time, which is attributed to the continuing hydration process. Thus, characterization of the hydration process provides an alternative approach for determining concrete strength. Various indirect methods can be used for this purpose, including calorimetry, thermal techniques, and nuclear magnetic resonance spectroscopy, which are generally expensive and require sophisticated methods of data analysis. Alternative approaches, such as ultrasound, are based on measurement of ultrasonic velocity, which is more related to concrete modulus and was applied to study the initial setting of concrete. There are also other empirical approaches based on the relationship between concrete strength and porosity. All these approaches, while working under certain situations, have shortcomings with respect to field applications. Accordingly, there still remains a need for a technique that accurately predicts compressive strength of concrete within a short period of time after placing that is non-destructive and economical.

SUMMARY OF THE INVENTION

The present invention relates to a method and apparatus for testing concrete using the principle of time domain reflectometry (TDR) associated with electromagnetic waves traveling in a medium. Two pieces of information may be obtained from the TDR signal in accordance with certain aspects of this invention. One aspect of the invention makes use of the relationship between apparent dielectric constant and gravimetric water content, and another aspect of the invention makes use of the relationship between electrical conductivity and compressive strength.

According to one aspect of the present invention, a method of measuring water content of concrete applies an electrical signal suitable for time domain reflectometry to a plurality of spikes placed in the concrete and analyzes a reflected time domain reflectometry signal to determine an apparent dielectric constant. The gravimetric water content of the concrete is then calculated using a predetermined relationship between the apparent dielectric constant and a ratio including density of water and total density of the concrete.

According to another aspect of the present invention, a method of measuring water-cement ratio of concrete applies an electrical signal suitable for time domain reflectometry to a plurality of spikes placed in the concrete and analyzes a reflected time domain reflectometry signal to determine an apparent dielectric constant. The gravimetric water content of the concrete is then calculated using a predetermined relationship between the apparent dielectric constant and a ratio including density of water and total density of the concrete. The cement content may be determined from batch records or by other methods. The water-cement ratio is then calculated.

According to a further aspect of the present invention, a method of predicting compressive strength development of concrete applies an electrical signal suitable for time domain reflectometry to a plurality of spikes placed in the concrete and analyzes a reflected signal using time domain reflectometry to determine electrical conductivity of the concrete. The compressive strength is then calculated based on the electrical conductivity of the concrete.

According to another aspect of the present invention, a method of determining behavior of concrete applies an electrical signal suitable for time domain reflectometry to a plurality of spikes placed in the concrete and analyzes a reflected time domain reflectometry signal to determine an electrical property of the concrete. A physical property is then calculated using a predetermined relationship between the electrical property and time.

According to a further aspect of the present invention, an apparatus for measuring water content of concrete comprises a plurality of spikes adapted to be placed into the concrete, means for applying an electrical signal suitable for time domain reflectometry to the plurality of spikes, means for analyzing a reflected signal using time domain reflectometry to determine an apparent dielectric constant of the concrete, and means for calculating gravimetric water content of the concrete using a predetermined relationship between the dielectric constant and a ratio including density of water and total density of the concrete.

According to a still further aspect of the present invention an apparatus for predicting compressive strength development of concrete comprises a plurality of spikes adapted to be placed into the concrete, means for applying an electrical signal suitable for time domain reflectometry to the spike, means for analyzing a reflected signal using time domain reflectometry to determine electrical conductivity of the concrete, and means for calculating compressive strength of the concrete using a predetermined relationship between the electrical conductivity and time.

DETAILED DESCRIPTION OF THE PREFERRED EMBODIMENTS

Figure 1:
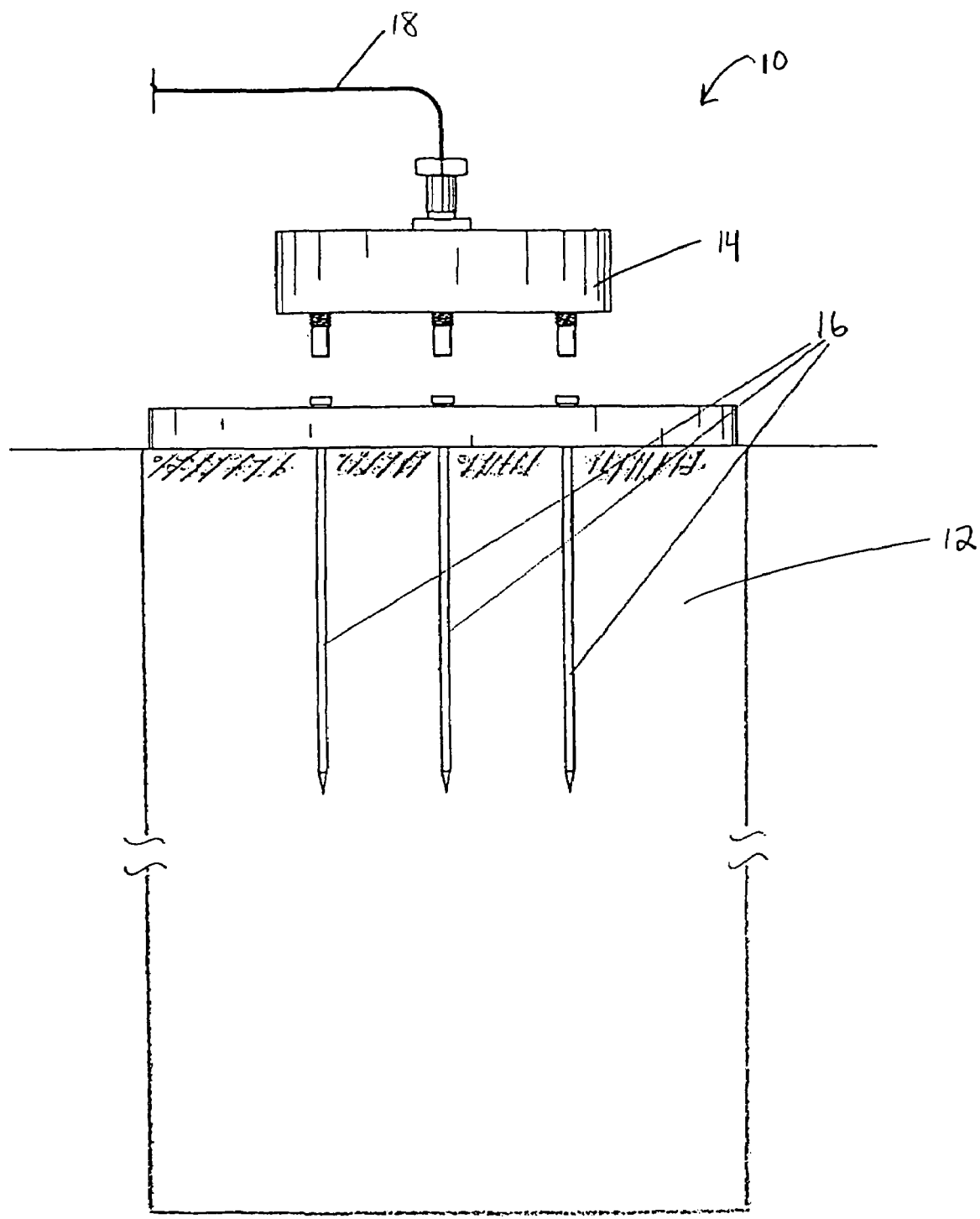
FIG. 1 is a side elevational view of a TDR apparatus of the present invention placed in concrete.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device and such further applications of the principles of the invention as illustrated therein being contemplated as would normally occur to one skilled in the art to which the invention relates.

A time domain reflectometry (TDR) apparatus 10 of the present invention, shown in FIG. 1, is used to measure electrical properties of the concrete 12. The apparatus 10 generally comprises a probe 14, a plurality of equally spaced spike sensors 16 (available at most local hardware stores), a coaxial cable 18, and a TDR tester (such as TDR100 tester available from Campbell Scientific, Inc., not shown). An apparatus of the type described above is described in more detail in U.S. Pat. No. 6,215,317 to Siddiqui et al., which patent is hereby incorporated by reference. Data collected by the TDR tester is analyzed in accordance with the present invention by a general purpose computer running a specially developed computer program that implements the equations described below.

Figure 2:
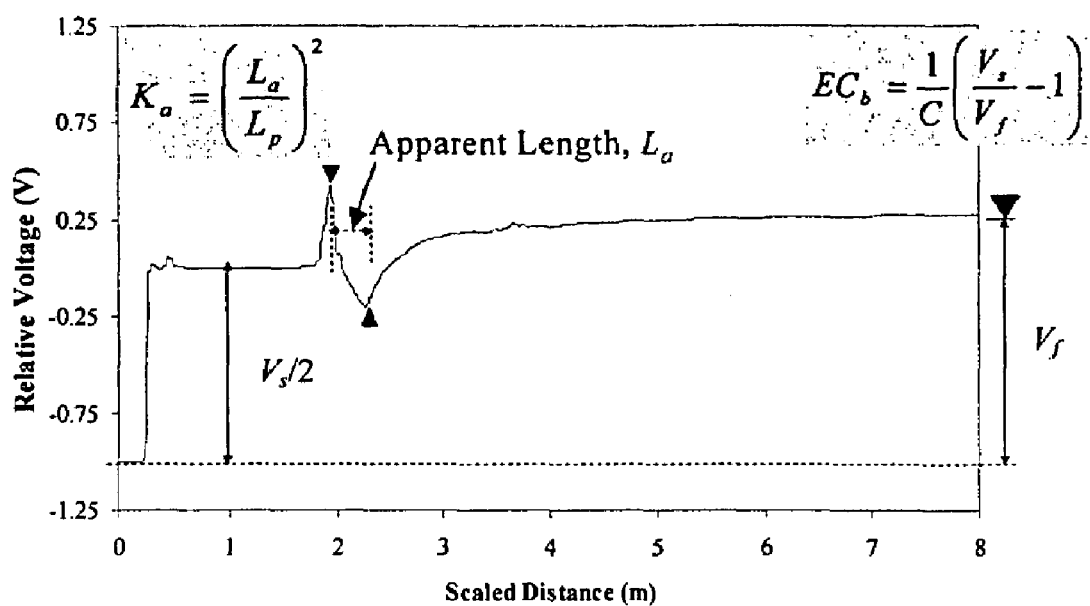
FIG. 2 shows the influence of material properties on a TDR waveform.

A typical TDR signal and information content for TDR measurement in a material is shown in FIG. 2. A "peak" and a "valley" are caused by reflections and are characteristic of TDR signals measured in geomaterials. The "peak" is caused by the first reflection, which occurs when the electromagnetic pulse crosses the air/material interface. The "valley" is caused by the second reflection, which occurs when the electromagnetic pulse arrives at the end of the measurement probe.

Dielectric constant, and electrical conductivity are two pieces of important information that can be obtained from analysis of a TDR signal. Material dielectric constant is analogous to Young's modulus in that it determines the electromagnetic wave speed. It can be determined from travel time analysis and is generally called apparent dielectric constant, denoted $K_a$. $K_a$ represents the real part of the frequency dependent dielectric permittivity. Equation (1) gives the mathematic expression for computing dielectric constant from TDR measurement.

$$K_a = \left(\frac{L_a}{L_p}\right)^2 \quad (1)$$

where $L_p$ is the length of the probe in the material and $L_a$ is the scaled horizontal distance between the two reflections, called apparent length.

The electrical conductivity, $EC_b$, causes attenuation of TDR signal and is another important piece of information that can be obtained from TDR waveforms. Different approaches can be used to obtain electrical conductivity from a TDR signal. Equation (2) uses an approach based on analysis of the long-term response of a TDR system to determine electrical conductivity.

$$EC_b = \frac{1}{C}\left(\frac{V_s}{V_f} - 1\right) \quad (2)$$

where $V_s$ is the source voltage, $V_f$ is the long term voltage level, and C is a constant related to probe configuration, determined from Equation (3) for coaxially configured probes, $$C = \frac{2\pi L_p R_s}{\ln\left(\frac{d_0}{d_i}\right)} \quad (3)$$

in which $L_p$ equals the length of the probe in the material, $R_s$ the internal resistance of the pulse generator (typically 50 ohms), and $d_o$ and $d_i$ are the diameters of outer and inner coaxial conductors, respectively.

Water plays an important role in concrete mixtures. It serves as a necessary agent for hydration reactions, in which free water molecules become chemically bound with cement particles. The amount of water involved in these reactions is typically only a fraction of the water added to the mixture. As the result, the major factor that controls the amount of water used in concrete is to provide a mixture that can be placed and is workable. Water in concrete mixtures comes from two main sources, i.e., water added during mixing process and the adsorbed water from aggregates. The moisture contents of coarse aggregates generally range from 0.5% to 2% and those of fine aggregates range from 2% to 6%, which can introduce a significant amount of water into the concrete mixture. Currently, there is no effective approach for field measurement of water content in freshly placed concrete.

The strong correlation between TDR-measured dielectric constant and the amount of water in concrete is attributed to the much larger dielectric constant of free water (around 81 at room temperature) as compared with the dielectric constant of air (around 1) or geomaterial solids (around 3 to 7).

Gravimetric water content and concrete dry densities can be related to concrete dielectric constant using Eq. (4).

$$\sqrt{K_a}\frac{\rho_w}{\rho_d} = a + bw \quad (4)$$

where a and b are concrete specific constants obtained from calibration tests.

For rapid determination of water content, a batch sample can be obtained and put into a cylindrical mold of known volume, from which total density of concrete in the mold, $\rho_t$, can be determined. The relationship between total density and dry density is given by Eq. (5)

$$\rho_d = \frac{\rho_t}{1+w} \quad (5)$$

Substituting Eq. (5) into Eq. (4) and solving for the water content gives:

$$w = \frac{\sqrt{K_a}\frac{\rho_w}{\rho_t} - a}{b - \sqrt{K_a}\frac{\rho_w}{\rho_t}} \quad (6)$$

Equation (6), with appropriate values of a and b for concrete, can be used to obtain the free water content of concrete.

Two different concretes were studied using a method of the present invention. The mixture proportions of the two concretes are shown in Table 1. The samples were obtained from field and put into standard 6'×12" plastic molds with volume of $6.107 \times 10^{-3}$ m$^3$. Additional samples were obtained to determine oven dry water content.

TABLE 1

Mixture proportions and water-cement ratio from batch mix records

| | Gravel (kg/m³) | Sand (kg/m³) | Cement (kg/m³) | Water (kg/m³) | Water-Cement ratio |
|---|---|---|---|---|---|
| Mixture 1 | 1089 | 916 | 306 | 162 | 0.52 |
| Mixture 2 | 1101 | 916 | 336 | 161 | 0.48 |

Water contents in concrete are computed from TDR-measured dielectric constant by Eq. (6). A temperature compensation factor (Eq. (7)) was applied before computing water content to compensate the effects of temperature on TDR-measured dielectric constant, based on a linear relationship observed between the value of apparent dielectric constant $K_a$ at a given temperature and the value of $K_a$ at a standard temperature, e.g. 20° C. Specifically, the value of $K_a$ obtained from the TDR signal at a given temperature is normalized to the standard temperature by multiplying the TDR-measured value of $K_a$ by a temperature compensation factor (TCF), where, for the above two concrete mixtures, $$TCF_{K_{ab}} = \frac{1}{0.0019 \cdot T + 0.952} \quad (7)$$

where T is temperature in ° C.

Physical interpretation as well as typical range of constants a and b are predominantly dependent on dielectric properties of dry solid phases and b being mostly decided by pore fluid. The values of constants a and b used in Eq.(6) for the concrete tested were set to a=1.0 and b=14.5.

A summary of measured water contents by TDR for the fresh concrete samples are shown in Table 2. There are several observations from this table. For both of these concretes, the oven dry water content is slightly larger than the water contents calculated from batch receipts (0.4% (for Mixture 2) and 0.3% (for Mixture 1)). These are equivalent to aggregates moisture content of 0.6% and 0.8% respectively, which are at the lower end of typical moisture range of aggregates discussed above. It is expected that the effects of aggregate moisture could be much more pronounced in other situations.

Table 2 shows Eq. (6) provides better accuracy for water content measurement in concrete than from what can be determined from batch records because it accounts for moisture content contained in aggregate used in the concrete mixtures.

TABLE 2

Water contents by TDR method

| Concrete Source | Dry Density (kg/m³) | Oven Dry Water Content (%) | Water Content from Batch Weights (%) | Eq. (6) (%) |
| --- | --- | --- | --- | --- |
| Mixture 2 | 2041 | 7.4 | 7.0 | 7.5 |
| Mixture 1 | 2078 | 7.1 | 6.8 | 7.0 |

Water in concrete exists in two different types, i.e., free water and chemically bound water. These two types of water show significantly different dielectric behavior. It has been established that free water has relaxation frequency of around 18 GHz while the relaxation frequency for bound water is within MHz range. (Relaxation frequency is a term that is analogous to resonant frequency for vibrating systems.) The TDR system used in the present invention has an effective frequency into the low gigahertz range and is more sensitive to the amount of free water than to bound water. Thus, it is a more direct indicator of amount of free water in concrete. This makes TDR-measured dielectric constant more instructive and easier to interpret compared with the system used in the past.

Figure 3:
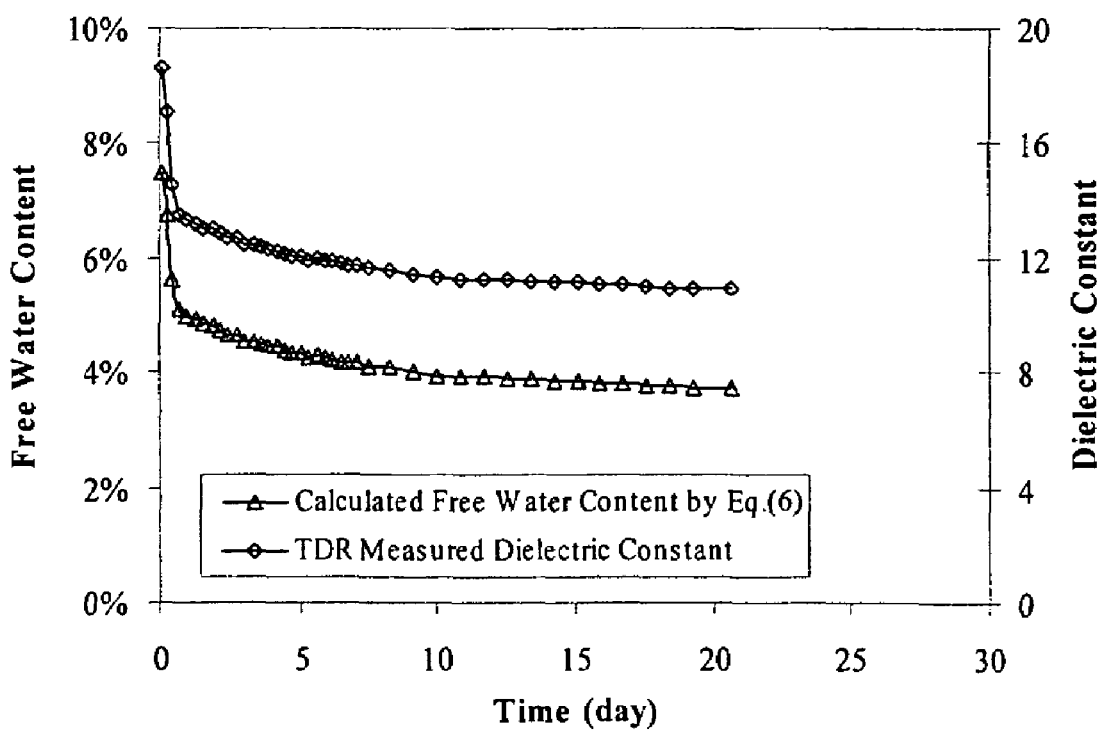
FIG. 3 shows TDR monitored free water content in concrete mixture 1.
Figure 4:
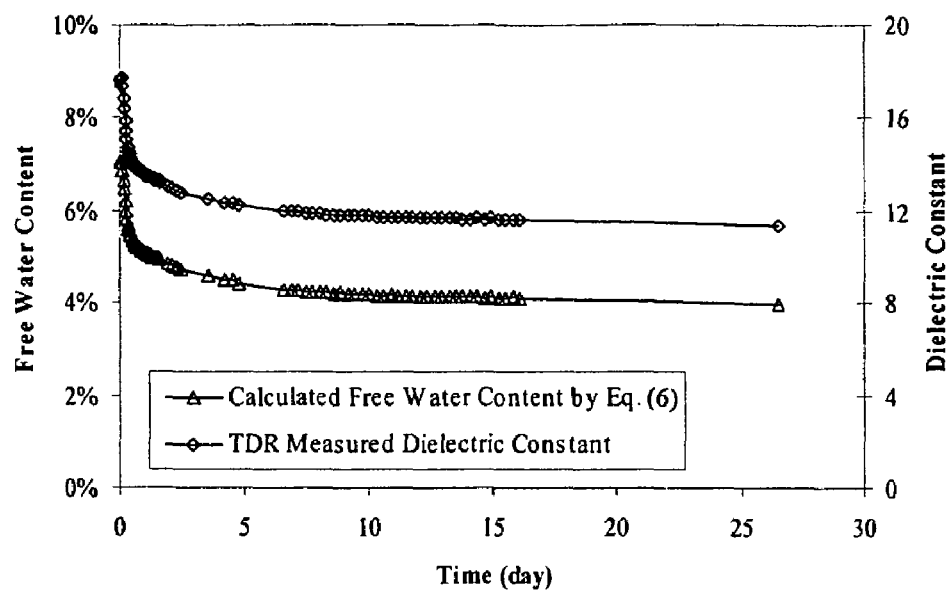
FIG. 4 shows TDR monitored free water content in concrete mixture 2.

The plots of TDR-measured dielectric constant with time are shown in FIGS. 3 and 4 for both concretes. The dielectric constant consistently decreased with time. The TDR measured dielectric constant decreases at a high rate at the initial stage, which indicates the high intensity of hydration reactions. The rate of decrease becomes smaller with time, which reflects reduced intensity of hydration. The free water contents calculated using equation Eq. (6) are also plotted in this figure, which clearly shows the decreasing amount of free water in concrete with time. After 196 days, the free water content in concrete sample Mixture 1 was around 3.0% and after 166 days Mixture 2 was around 3.5%. The fact that TDR measurements can be easily automated makes it an attractive tool for monitoring the free water content in concrete.

The TDR-measured water content can be combined with the information of cement content from batch receipts to make an estimate of water-cement ratio. The calculated water-cement ratio of concrete samples from Mixture 1 was 0.53 and that of Mixture 2 was 0.52, which are slightly higher than calculated from batch receipts (by 0.1 and 0.4), respectively. As mentioned before, the moisture contents of aggregates in these concretes are believed to be at the lower end of typical moisture content range. The resulting difference in water-cement ratio can be more significant for aggregates with higher water content or in situations where water is added at the job site.

While hydration causes the change of concrete mechanical structure and corresponding increase of concrete strength, it simultaneously changes concrete physico-chemical and electrical properties. Thus, electrical properties of concrete and mortar, especially the electrical conductivity, are strongly related to the strength of concrete.

While chemical reactions are the most important process occurring during concrete curing, the exact nature of the entire hydration process is complicated and not fully understood. Generally speaking, hydration reactions take place between cement powder and water upon mixing and theoretically, the process continues forever. Major products of the reactions include calcium silicate, calcium aluminate, ettringite, etc. Calcium silicate is the major component affecting concrete strength and calcium aluminates predominantly determine the time of initial setting. A significant amount of heat is generated during hydration process.

A direct consequence of the hydration process is a change in the microscopic structure. This results in the increase of modulus and strength. There is a strong linear correlation between concrete strength and degree of hydration. The hydration process, which significantly changes the microstructure of concrete, changes the electrical behavior of concrete as well. Bulk water becomes chemically bound water, which shows significantly different dielectric behavior compared with free bulk water. The formation of solid structures by hydration reactions reduces the amount of free ions in pore solution, which results in a decrease of electrical conductivity. Thus, concrete electrical behavior can be a strong indicator of the progress of the hydration process. As the hydration process directly results in the increase of concrete strength, electrical properties can thus be used to monitor strength development.

The dielectric properties of concrete are dependent on factors such as the amount of water in the pore system and the concrete microstructure. The measured results of dielectric properties are also influenced by electrode configuration and measurement frequency band. Optimized design, both in sensor geometry and measurement frequency range, is necessary to achieve the best measurement results.

Accurate measurement of dielectric properties of concrete is critical to achieving the best measurement accuracy. Various technologies and system designs can be used for this purpose, including technologies based on measurement of frequency dependant behavior as obtained with an impedance analyzer or network analyzer. While these systems collect more information, measurements are generally expensive and data analysis is difficult. Such systems typically are not suitable for field applications.

In addition to automatically monitoring dielectric properties of the two concrete mixtures with time, strengths at 1 day, 7 days, and 28 days also were measured using specimens collected at the time of concrete placing. The compressive tests were performed in certified laboratories.

Figure 5:
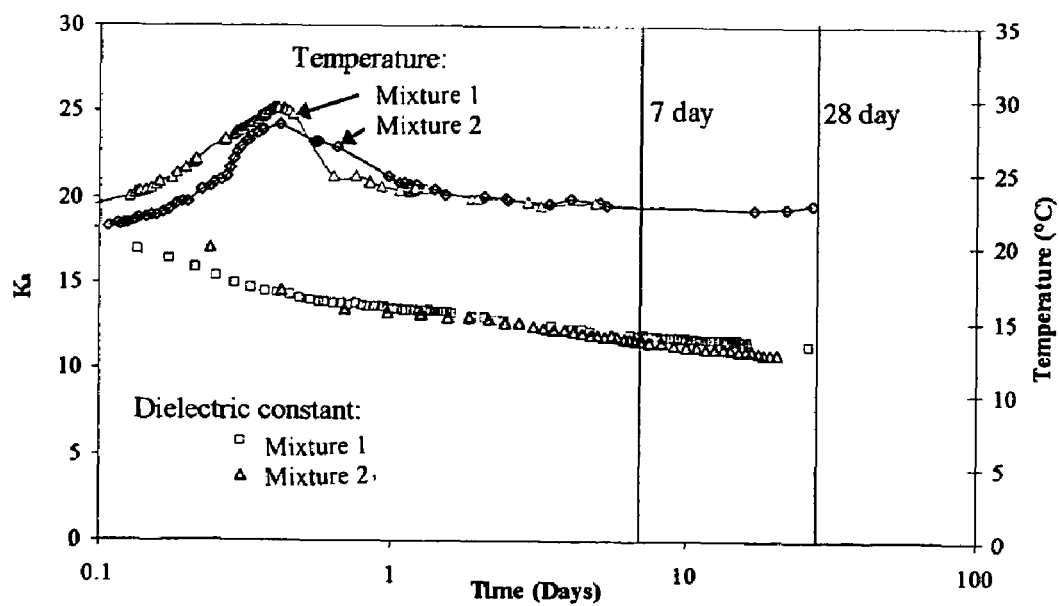
FIG. 5 shows changing dielectric properties and temperature of the concrete mixtures over time.
Figure 6:
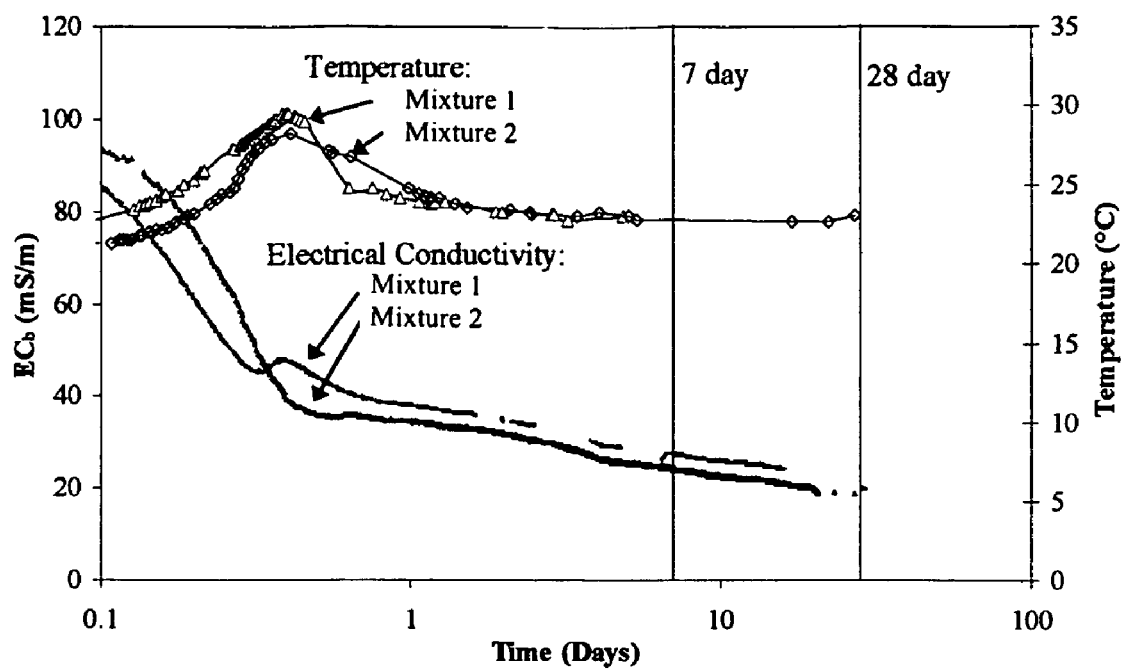
FIG. 6 shows changing electrical conductivity and temperature of the concrete mixtures over time.

FIGS. 5 and 6 show how the dielectric properties, electric conductivity and dielectric constant, change with time. Dielectric constant consistently decreases with time, which is an indication of the decreasing amount of free water in concrete. Due to hydration reactions, free water becomes chemically bound water, which has much smaller dielectric constant than free water. The observed changes of dielectric constant shown in FIG. 5 are different from previous study results that found the dielectric constant first increases and then decreases with time. Since the frequency used in previous studies were within the relaxation frequency range of chemically bound water, measurements were sensitive to the behaviors of both free water and chemically bound water. The previously observed increase of dielectric constant at the initial stage was the result of the dominant role played by the increasing amount of bound water. The decrease of dielectric constant in the longer term was dominated by the decreasing amount of free water. While previous studies helped to explain mechanisms of hydration in the fresh concrete mixture, they also caused difficulty in the interpretation of results since effects of bound water and free water could not be separated. The effective measurement frequency of the TDR tester used in the present invention is in the low Gigahertz range, which is beyond the relaxation frequency of bound water. Thus, the dielectric constant measured by TDR is predominantly influenced by the amount of free water in concrete. This makes the measurement much easier to interpret since the reduced amount of free water reflects the increased amount of bound water.

The decrease of electrical conductivity as shown in FIG. 6 is more significant, as it provides a strong indication of the structural changes and reduced amount of free ions in the concrete. The data for the initial part of the test in FIG. 6 is replotted with an arithmetic time scale to show the behavior of freshly mixed concrete in FIG. 7. The electrical conductivity increases slightly after the mixing (FIG. 7), which possibly is caused by effects of consolidation and particle rearrangement.

Another important observation from FIG. 6 is that for both of these concrete samples, after completion of the initial stages, the change of electrical conductivity decreases linearly with the logarithm of time. The slope of this line, which is believed to be related to rate of hydration, is similar for both concretes. At any given time after the initial stages, the electrical conductivity of the Mixture 2 concrete is smaller than that of Mixture 1 concrete.

Figure 7:
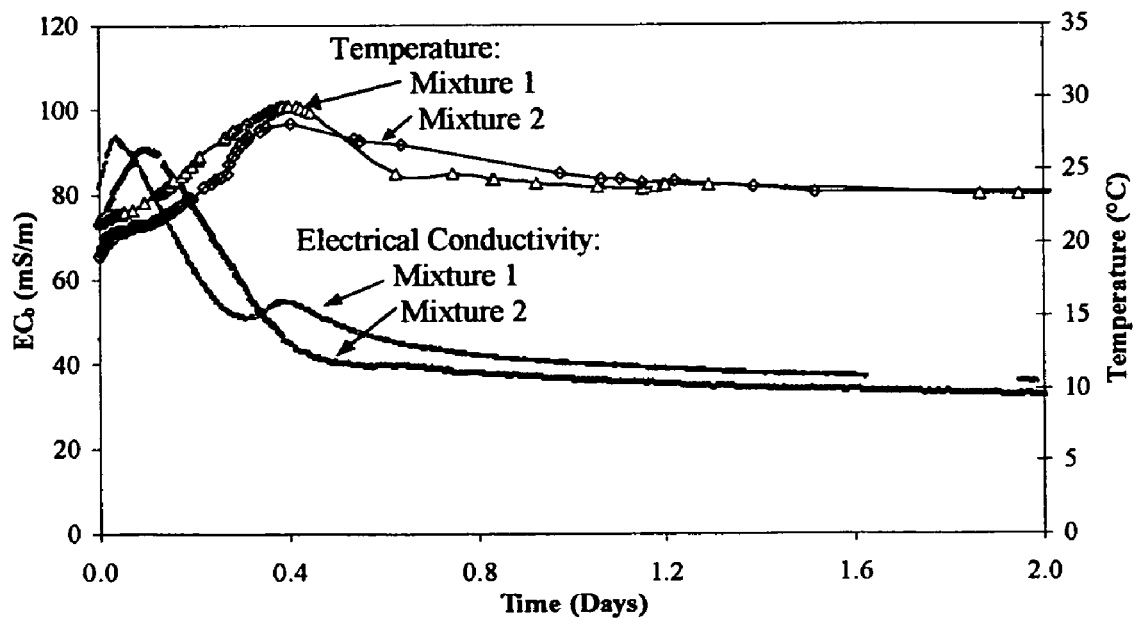
FIG. 7 shows the data of FIG. 6 replotted with an arithmetic time scale.

From FIGS. 5-7, we can see that the temperature curves of the two concretes are similar. A group of tests were performed to investigate the effects of temperature on TDR measured dielectric constant and electrical conductivity. The cured concrete specimens from both mixtures were sealed and stored for 24 hours in temperature controlled room of 4° C. and 40° C., respectively, and then allowed to return to ordinary laboratory room temperature. As the mixture temperature was being restored to room temperature, TDR and thermocouple readings were taken to monitor the change of dielectric constant and electrical conductivity with temperature.

Figure 8:
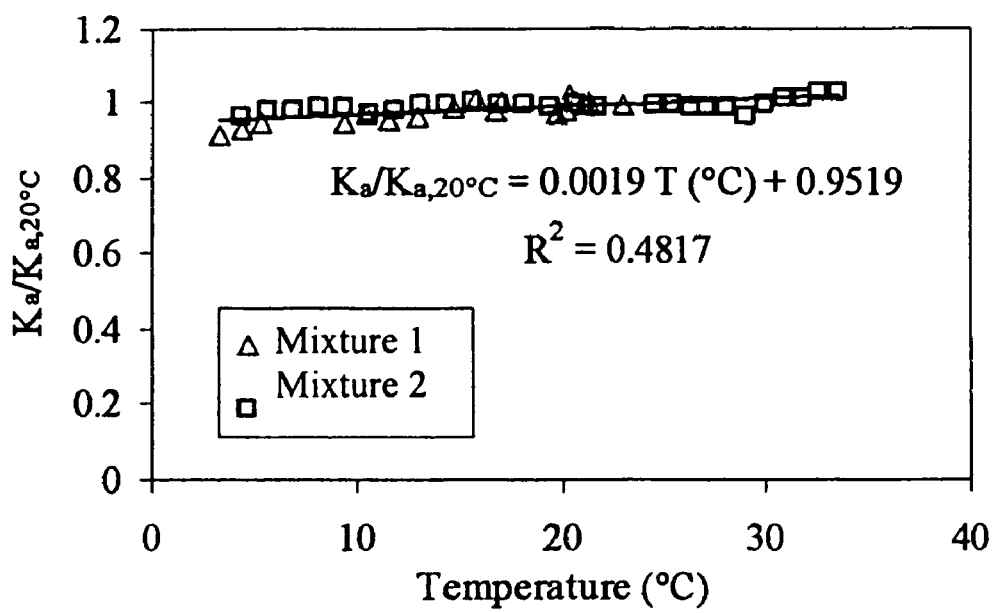
FIG. 8 shows the effect of temperature on TDR measured dielectric constants of concrete.
Figure 9:
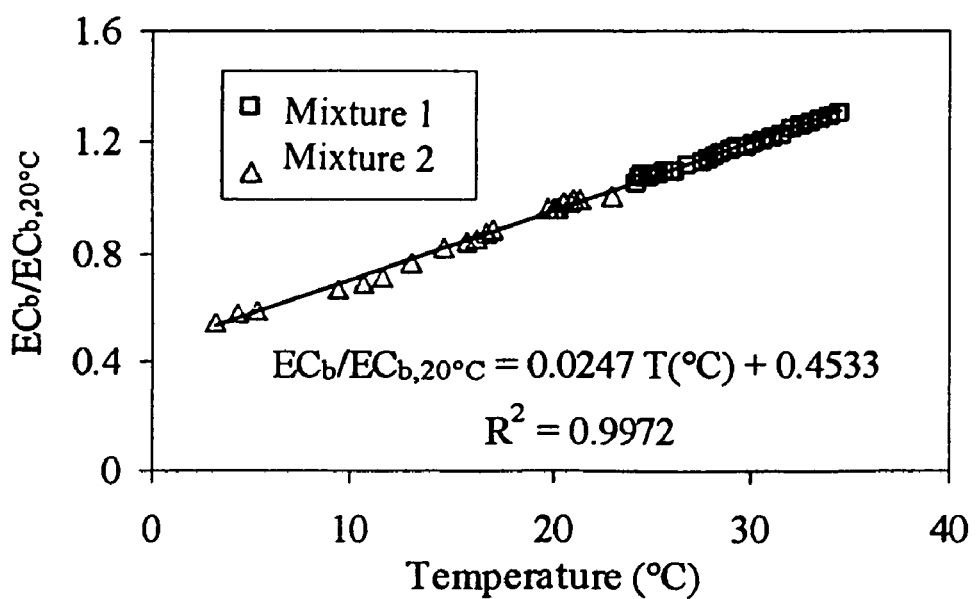
FIG. 9 shows the effect of temperature on TDR measured electrical conductivity of concrete.

The measured values of dielectric constant and electrical conductivity for the two mixtures are normalized by those at room temperature (22° C.) and are plotted in FIGS. 8 and 9. FIGS. 8 and 9 show that both the dielectric constant and electrical conductivity increase linearly with temperature within the temperature range of the study. The effect of temperature on electrical conductivity measurement is much more significant than that of dielectric constant as indicated by the steeper slope in FIG. 9.

From these observations, the following temperature compensation factors (Eq.(8)) are recommended to compensate for the effects of temperature on TDR measured dielectric constant and electrical conductivity.

$$TCF_{K_a} = \frac{1}{0.0019 \cdot T + 0.952} \qquad (8)$$

$$TCF_{EC_b} = \frac{1}{0.0247 \cdot T + 0.453}$$

where T is temperature in ° C.

Figure 10:
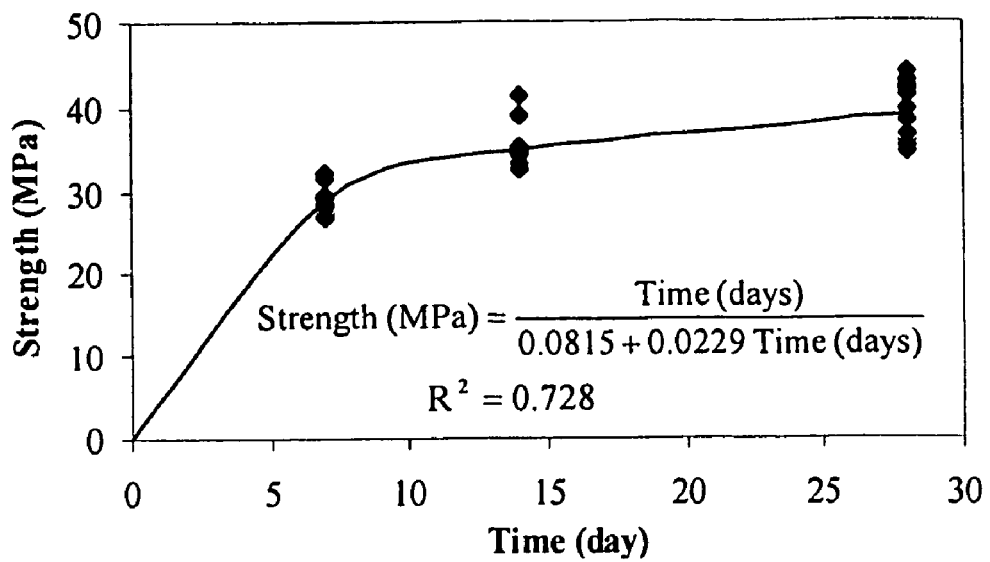
FIG. 10 shows compressive strength results from Mixture 1 concrete cylinder testing.
Figure 11:
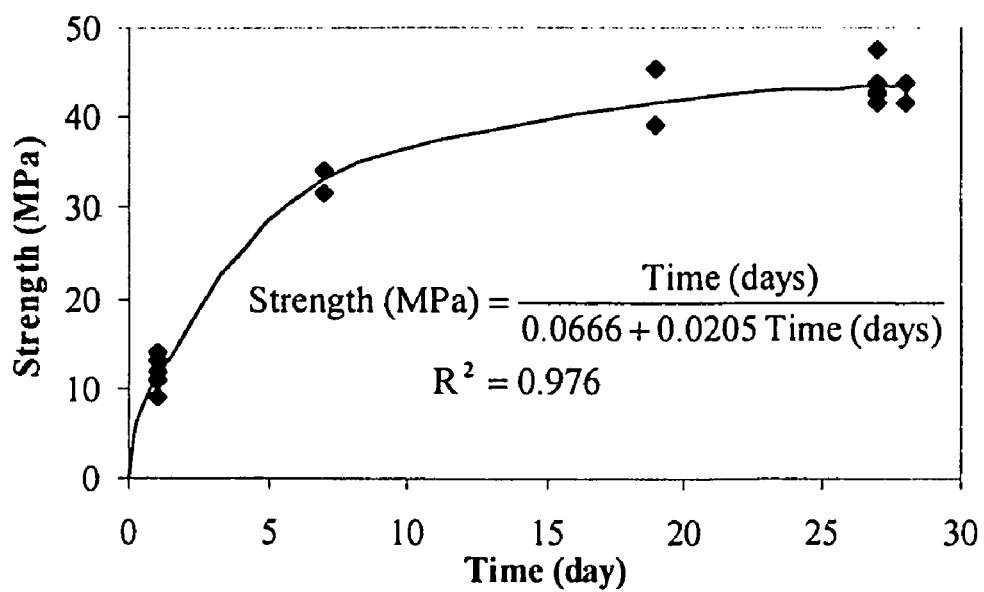
FIG. 11 shows compressive strength results from Mixture 2 concrete cylinder testing.

The results of compressive strength obtained from concrete cylinder testing are shown in FIGS. 10 and 11. There is significant (about 20%) although not unreasonable scatter of results, which is possibly due to effects of sampling disturbance and curing process. The phenomena are common when evaluating concrete strength from cylinder samples. Hyperbolic curves give good fit to the data and can be used to describe the evolution of compressive strength with time.

Figure 12:
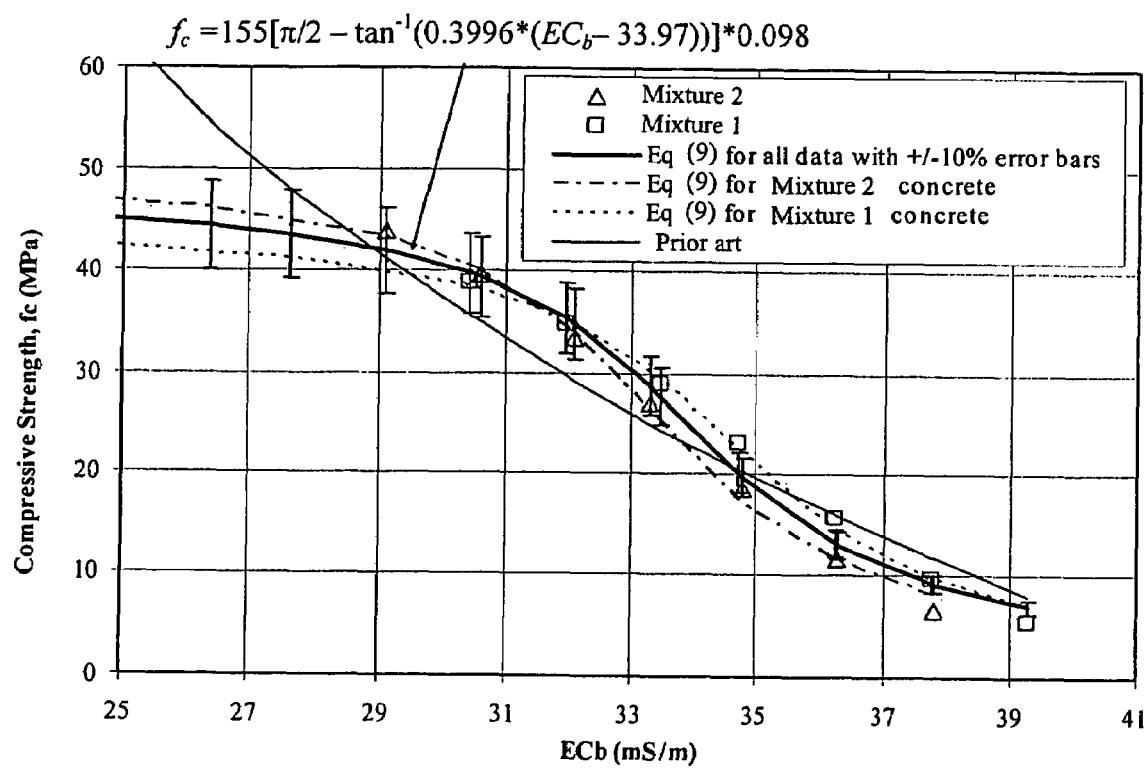
FIG. 12 shows the relationship between TDR measured electrical conductivity and compressive strength for both concretes.

The compressive strengths at different curing times predicted by the hyperbolic curves in FIGS. 10 and 11 are plotted against the temperature compensated TDR measured electrical conductivity in FIG. 12. FIG. 12 indicates that the compressive strengths show reverse relationships with electrical conductivity, which are similar for the two concretes tested.

These curves show linear trend in the middle and are slightly curved at high electrical conductivities (initial stage) and at low electrical conductivities (long term). The reverse trend between concrete strength and electrical conductivity is believed to be valid since the hydration process reduces the amount of free ions in concrete (and thus reduces the electrical conductivity) and at the same time increases its compressive strength.

It is observed that a curve in the form of Eq. (9) gives good fit to the data in FIG. 12 and gives the reasonable strength values for extreme conditions.

$$f_c = \alpha \left[ \frac{\pi}{2} - \tan^{-1}(\beta(EC_b - EC_0)) \right] P_a \qquad (9)$$

where $f_c$ is compressive strength (same units as $P_a$); $\alpha$ is an empirical constant (no units), $\beta$ is an empirical constant (units of m/mS), and $EC_0$ (units of mS/m) are obtained from calibration tests; the term $EC_b$ (in units of mS/m) is TDR measured electrical conductivity after temperature compensation by Eq. (8); and $P_a$ is the atmospheric pressure ($P_a$=0.098 MPa for SI units and $P_a$=14.7 lb/in$^2$ for U.S. Customary units).

Using Eq. (9), three curves are plotted in FIG. 12, one for Mixture 2 concrete, one for Mixture 1 concrete, and one for both concretes combined. The equation for the curve for the combined data and corresponding error bars of ±10% are given in the figure by the darker solid line. The combined data were also used with equations recommended in the prior art, also shown in FIG. 12, having a concave upward shape.

From FIG. 12 it can be seen that fitted curve by Eq. (9) gives reasonable estimation of compressive strength from TDR measured electrical conductivity. The estimated strength generally falls within ±10% of the optimized compressive strengths from cylinder tests. Equations recommended in the prior art on the other hand cannot accurately describe the data trend, especially at low electrical conductivity (corresponding to long term strength). The measured electrical conductivity for Mixture 1 concrete was 11.96 mS/m after 196 days and that of Mixture 2 is 11.95 mS/m after 166 days. The estimated strengths by Eq. (9), using the parameters obtained from the combined data, are 47.6 MPa and 47.6 MPa, respectively. Equations recommended in the prior art on the other hand, gives unreasonable estimated strengths of 225.0 MPa and 224.7 MPa, respectively. Thus, Eq. (9) is believed to be more robust for estimating compressive strength from electrical conductivity.

To apply Eq. (9), a group of calibration tests are needed to determine the calibration constants. The calibration involves making several cylinders for a given mix design. For one of the cylinders, the TDR probe and a temperature sensor are installed to monitor the dielectric constant, electrical conductivity, and temperature with time. Compression tests are performed on the other cylinders to determine compressive strength at different ages, typically one day, seven days, and twenty eight days. The compressive strength and temperature compensated electrical conductivity are then analyzed in a spreadsheet to obtain the calibration constants in Eq. (9). Once the calibrations are obtained, the measured electrical conductivity, either in the field or in the laboratory, can be applied to estimate the compressive strength.

FIG. 6 shows that the electrical conductivity linearly decreases with time on a logarithmic scale after about one day, which is similar for both concretes. This can be described by Eq. (10).

$$EC_b(t) = EC_b(t_1) + \left(\frac{\Delta EC_b}{\log \text{cycle}}\right)\log(t) \qquad (10)$$

where: t is the curing time in days, $EC_b(t_1)$ is the electrical conductivity measured at one day, $\Delta EC_b/(\log \text{cycle})$ is the change in electrical conductivity over one log cycle, all in units of mS/m. For Mixture 1 concrete, the corresponding values of $EC_b(t_1)$ and $\Delta EC_b/(\log \text{cycle})$ are 37.75 mS/m and −5.05 mS/m, respectively. The corresponding values for Mixture 2 concrete are 36.29 mS/m and −4.96 mS/m, respectively. Note that t in Eq. (10) may have decimal values, but that values of t must not be smaller than the linear portion of the curve on the log-time plot used to establish the coefficients. For example, for the Mixture 2 curve in FIG. 6, the value of t must be greater than approximately 0.5 days.

Once its relationship with time is established, the electrical conductivity measured at curing times sufficiently long to establish the straight line on the semi-log plot could be used to estimate long-term electrical conductivity, and consequently, the long-term compressive strength by combining Eqs. (9) and (10) as shown in Eq. (11).

$$f_c = \alpha\left[\frac{\pi}{2} - \tan^{-1}\left\{\beta\left[EC_b(t_1) + \left(\frac{\Delta EC_b}{\log \text{cycle}}\right)\log(t) - EC_0\right]\right\}\right]P_a \qquad (11)$$

where the parameters are defined above for Eqs. (9) and (10).

Figure 13:
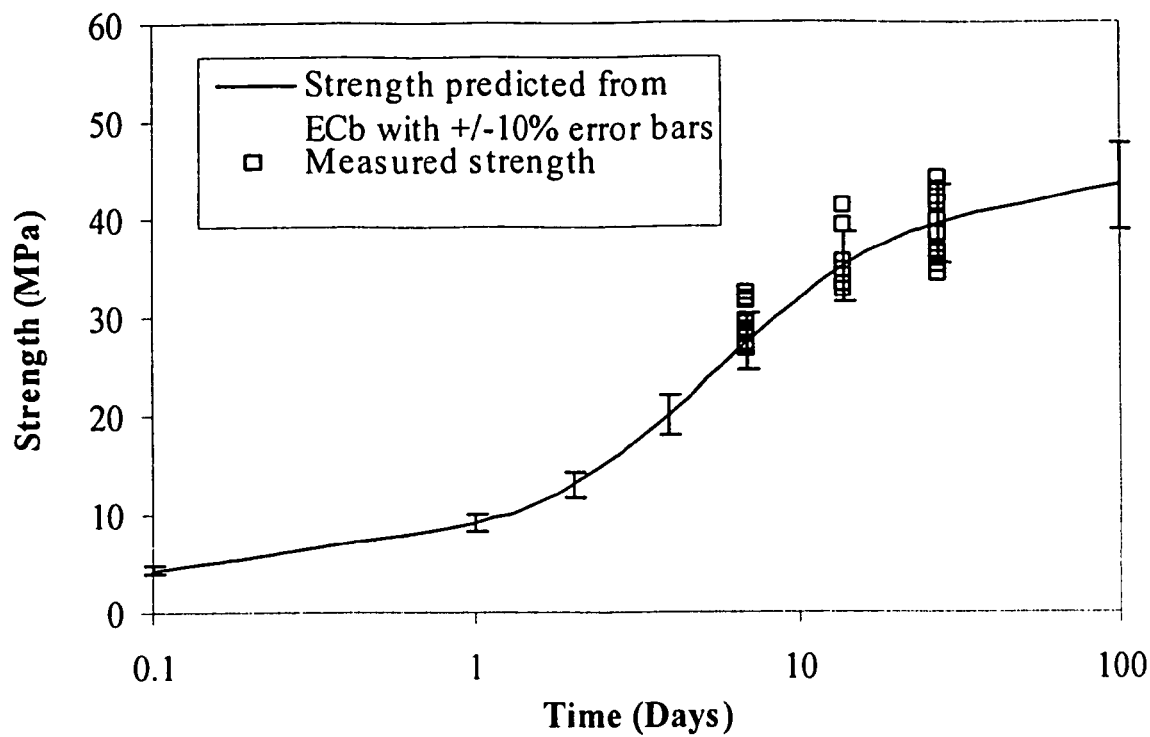
FIG. 13 shows estimated compressive strength of Mixture 1 using a method of the present invention compared to actual measurements.
Figure 14:
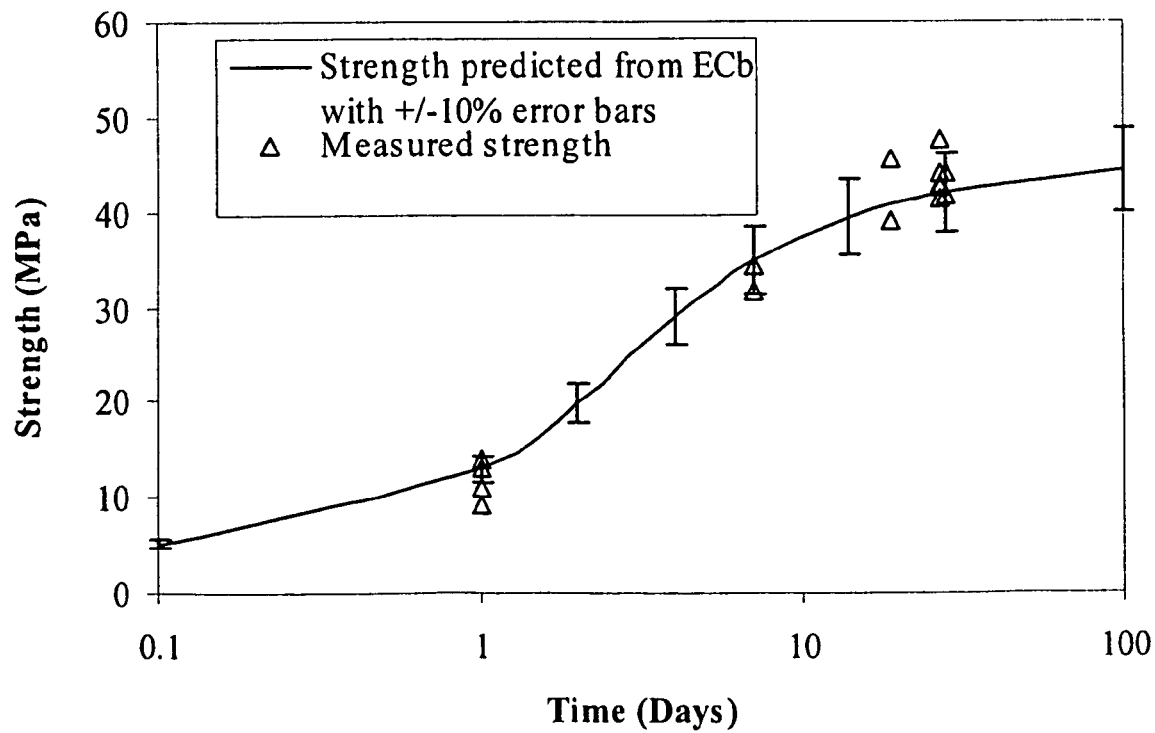
FIG. 14 shows estimated compressive strength of Mixture 2 using a method of the present invention compared to actual measurements.

FIGS. 13 and 14 show the predicted compressive strength versus time in days (log scale) by Eq. (11) for both Mixture 1 concrete and Mixture 2 concrete. The parameters used in Eq. (11) to predicted these curves are summarized in Table 3, where the values of αβ, and $EC_0$ are from the equation shown in FIG. 12 (solid curve with the thick line) and the values of $EC_b(1 \text{ day})$ and $\Delta EC_b(\text{per log cycle})$ are from fitting the straight lines through the linear portion in FIG. 6 for each of the concrete samples. The actual measured compressive strengths are also plotted for comparison. They generally fall within ±10% of predicted strength. Even though these curves are based on tests only up to 28 days, FIGS. 13 and 14 indicates that the longer term strengths given by Eq. (11) appear quite reasonable.

TABLE 3

Parameters of Eq. (11) for curves in FIGS. 13 and 14

| | | |
|---|---|---|
| α | 155 | |
| β (m/mS) | 0.3996 | |
| $EC_0$ (mS/m) | 33.97 | |
| Concrete | Mixture 1 | Mixture 2 |
| $EC_b(t_1)$ (mS/m) | 37.75 | 36.29 |
| $\Delta EC_b$/log cycle (mS/m) | −5.05 | −4.96 |

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of measuring water content of concrete, comprising the steps of:
    placing a plurality of spikes into the concrete;
    applying to said plurality of spikes an electrical signal suitable for time domain reflectometry;
    analyzing a reflected signal using time domain reflectometry to determine an apparent dielectric constant $K_a$ of the concrete;
    calculating gravimetric water content w of the concrete using a predetermined relationship between $K_a$ and a ratio including density of water $P_w$ and total density of the concrete $P_t$; and
    outputting a result of said calculation.

2. The method of claim 1, wherein said predetermined relationship between $K_a$ and said ratio including density of water $P_w$ and total density of the concrete $P_t$ is $$w = \frac{\sqrt{K_a}\frac{\rho_w}{\rho_t} - a}{b - \sqrt{K_a}\frac{\rho_w}{\rho_t}},$$

where a and b are concrete specific calibration constants.

3. The method of claim 2, wherein said apparent dielectric constant $K_a$ is adjusted to compensate for temperature.

4. The method of claim 3, wherein said adjustment to compensate for temperature comprises adjusting said apparent dielectric constant $K_a$ based upon a linear relationship between $K_a$ at a given temperature and $K_a$ at a reference temperature.

5. The method of claim 1, wherein said electrical signal has a frequency above a relaxation frequency of bound water in the concrete.

6. A method of measuring water-cement ratio of concrete, comprising the steps of:
    placing a plurality of spikes into the concrete;
    applying to said plurality of spikes an electrical signal suitable for time domain reflectometry;
    analyzing a reflected signal using time domain reflectometry to determine an apparent dielectric constant $K_a$ of the concrete;
    calculating gravimetric water content w of the concrete using a predetermined relationship between $K_a$ and a ratio including density of water $P_w$ and total density of the concrete $P_t$;
    determining the cement content C;
    calculating water-cement ratio of the concrete; and
    outputting a result of said water-cement ratio calculation.

7. The method of claim 6, wherein said predetermined relationship between $K_a$ and said ratio including density of water $P_w$ and total density of the concrete $P_t$ is $$w = \frac{\sqrt{K_a}\frac{\rho_w}{\rho_t} - a}{b - \sqrt{K_a}\frac{\rho_w}{\rho_t}},$$

where a, and b are concrete specific calibration constants.

8. The method of claim 7, wherein said apparent dielectric constant $K_a$ is adjusted to compensate for temperature.

9. The method of claim 8, wherein said adjustment to compensate for temperature comprises adjusting said apparent dielectric constant $K_a$ based upon a linear relationship between $K_a$ at a given temperature and $K_a$ at a reference temperature.

10. The method of claim 6, wherein said electrical signal has a frequency above a relaxation frequency of bound water in the concrete.

11. A method of predicting compressive strength development of concrete, comprising steps of:
   placing a plurality of spikes into the concrete;
   applying to said plurality of spikes an electrical signal suitable for time domain reflectometry;
   analyzing a reflected signal using time domain reflectometry to determine electrical conductivity $EC_b$ of the concrete;
   predicting compressive strength $f_c$ of the concrete based upon $EC_b$ decreasing log-linearly in time; and
   outputting a result of said prediction.

12. A method of predicting compressive strength development of concrete, comprising steps of:
   placing a plurality of spikes into the concrete;
   applying to said plurality of spikes an electrical signal suitable for time domain reflectometry;
   analyzing a reflected signal using time domain reflectometry to determine electrical conductivity $EC_b$ of the concrete;
   predicting compressive strength $f_c$ based upon a predetermined relationship of $$f_c = \alpha \left[ \frac{\pi}{2} - \tan^{-1} \left\{ \beta \left[ EC_b(t_1) + \left( \frac{\Delta EC_b}{\log \text{cycle}} \right) \log(t) - EC_0 \right] \right\} \right] P_a,$$

where $\alpha$ is an empirical constant, $\beta$ is an empirical constant, $EC_b(t_1)$ is said electrical conductivity $EC_b$ measured at one day, $\Delta EC_b/(\log \text{cycle})$ is change in said electrical conductivity over one log cycle, $EC_0$ is obtained from calibration tests, and $P_a$ is atmospheric pressure; and
   outputting a result of said prediction.

13. The method of claim 12, wherein said electrical conductivity $EC_b$ is adjusted to compensate for temperature.

14. The method of claim 13, wherein said adjustment to compensate for temperature comprises adjusting said electrical conductivity $EC_b$ based upon a linear relationship between $EC_b$ at a given temperature and $EC_b$ at a reference temperature.

15. An apparatus for measuring water content of concrete, comprising:
   a plurality of spikes adapted to be placed into the concrete;
   means for applying to said plurality of spikes an electrical signal suitable for time domain reflectometry;
   means for analyzing a reflected signal using time domain reflectometry to determine an apparent dielectric constant $K_a$ of the concrete;
   means for calculating gravimetric water content w of the concrete using a predetermined relationship between $K_a$ and a ratio including density of water $P_w$ and total density of the concrete $P_t$; and
   means for outputting a result of said calculation.

* * * * *